US009976986B2

(12) United States Patent
Wayman et al.

(10) Patent No.: US 9,976,986 B2
(45) Date of Patent: May 22, 2018

(54) PIPELINE CONDITION DETECTING APPARATUS AND METHOD

(71) Applicant: Advanced Engineering Solutions Ltd., Cramlington Northumberland (GB)

(72) Inventors: Malcolm Wayman, Cramlington (GB); Richard Treece, Cramlington (GB)

(73) Assignee: Advanced Engineering Solutions Ltd., Cramlington, Northumberland (GB)

( * ) Notice: Subject to any disclaimer, the term of this patent is extended or adjusted under 35 U.S.C. 154(b) by 0 days. days.

(21) Appl. No.: 15/027,325

(22) PCT Filed: Oct. 14, 2014

(86) PCT No.: PCT/GB2014/053080
§ 371 (c)(1),
(2) Date: Apr. 5, 2016

(87) PCT Pub. No.: WO2015/055995
PCT Pub. Date: Apr. 23, 2015

(65) Prior Publication Data
US 2016/0245780 A1     Aug. 25, 2016

(30) Foreign Application Priority Data
Oct. 14, 2013   (GB) .................................. 1318096.3

(51) Int. Cl.
*G01N 27/82*     (2006.01)

(52) U.S. Cl.
CPC .................................. *G01N 27/82* (2013.01)

(58) Field of Classification Search
CPC ................................ G01N 27/82; G01N 27/72
See application file for complete search history.

(56) References Cited

U.S. PATENT DOCUMENTS

| 4,763,070 A * | 8/1988 | Huschelrath ........... G01N 27/82 324/225 |
| 5,151,649 A * | 9/1992 | Heroux ................. G01R 15/18 324/117 R |
| 2003/0011363 A1* | 1/2003 | Wayman ................ G01N 27/82 324/238 |
| 2004/0041560 A1* | 3/2004 | Walters ................. G01N 27/82 324/238 |
| 2010/0207620 A1* | 8/2010 | Gies ................... G01N 27/9033 324/240 |
| 2010/0300184 A1* | 12/2010 | Wayman ................. F17D 5/00 73/73 |

FOREIGN PATENT DOCUMENTS

| CN | 102654479 A | 9/2012 |
| EP | 0193168 A2 | 9/1986 |
| EP | 1262771 A2 | 12/2002 |
| GB | 1567166 A | 5/1980 |
| JP | H04 269653 A | 9/1992 |
| WO | WO 2013128212 A1 | 9/2013 |

* cited by examiner

*Primary Examiner* — Tung X Nguyen
*Assistant Examiner* — Adam Clarke
(74) *Attorney, Agent, or Firm* — Gable Gotwals

(57) ABSTRACT

This invention relates to an apparatus and method for detecting the condition of a pipeline wall and analysis and estimate of the life of the pipeline by using an apparatus mounted externally of the pipeline and provided to be moved about and/or along at least a portion of the same. The apparatus includes at least one sensor array which includes a plurality of sensors axially offset to provide data for analysis and identification of pipeline defects.

19 Claims, 8 Drawing Sheets

Scan Plot of Axial Corrosion with SmartCAT™

PIPELINE CONDITION DETECTING APPARATUS AND METHOD

CROSS-REFERENCE TO RELATED APPLICATIONS

This application is the United States National Phase of Patent Application No. PCT/GB2014/053080 filed 14 Oct. 2014, which claims priority to British Patent Application No. 1318096.3 filed 14 Oct. 2013, each of which are incorporated herein by reference.

BACKGROUND OF THE INVENTION

The invention to which this application relates is the provision of apparatus and a method for detecting the condition of a pipeline wall and analysis and estimate of the life of the pipeline.

It is known to provide apparatus which can be used to assess the quality, damage, and/or risk of failure of pipelines which have been in service for a period of time and, from the information provided by the apparatus and method, to then assess whether the pipeline is in a potentially dangerous condition or needs specific maintenance to be undertaken and/or can allow scheduled maintenance to be planned and performed on the basis of the detected information. This therefore avoids the need for the pipeline to be unnecessarily completely replaced and/or ensures that if the pipeline is in a dangerous state of decay, this can be identified with the pipeline in situ and without the need to first extensively excavate the pipe and repair or replace the same.

A known detection apparatus is typically known as a "pig", which is passed along the interior of the pipeline with the apparatus being carried by the flow of the gas or liquid as it flows along the pipeline interior. As the pig passes along the interior of the pipe, results from detection means mounted on the apparatus allows a survey to be formed of the pipeline condition. However, a problem is that this type of apparatus is not always suitable or compatible with particular liquids or gases which pass along the pipeline interior due to fears of contamination and/or safety risk. Thus, the use of internally located and moving pigs is generally regarded as being impractical or potentially dangerous, may affect the quality of some liquids passing along the pipeline and also the results obtained from the same can be inferior or not sufficiently accurate to allow a reliable survey of the pipeline to be created.

It is also known to provide apparatus which can travel along the exterior surface of a pipeline. This form of apparatus can be provided with means to allow the same to be moved along the exterior of the pipeline.

In one embodiment a magnetic flux is generated which passes into the pipeline. As the apparatus moves along the pipeline, the level of the magnetic flux is monitored to ensure that any changes in flux are detected. This change can be caused by "leakage" and is indicative of reduced pipe wall thicknesses. As a result, the possible corrosion or damage to the pipe wall is indicated and mapped with respect to the position of the apparatus on the pipeline.

With many types of pipeline, this form of apparatus can be satisfactory in that the magnetic flux indicates the position of a defect and a subsequent inspection of the external surface of the pipeline indicates to the user whether the defect is on the external surface of the pipeline. If the defect is visible then magnetic flux can be used to determine the depth of the fault but, if the defect is not visible, the fault is then assumed to be on the interior wall of the pipeline and the magnetic flux change can again be used to determine the size and depth of the fault. This apparatus is therefore available for use where a visual check of the external pipeline can be used to determine the position of the defect indicated by a magnetic flux change.

However, with certain materials, such as for example cast iron, there may be defects on or near the exterior of the pipe which are not visible and therefore the conventional apparatus cannot be used, as a visual check of the external surface is not guaranteed to identify whether or not an external or internal defect is present. In order to overcome this problem it is known to provide apparatus which includes both Hall effect sensors and proximity sensors to allow both the magnetic flux and change in condition of the pipeline wall to be detected. The applicant's copending application EP1262771 describes one form of such apparatus.

In practice it has been found that it is desirable to be able to identify and optimize the sizing of pipe wall defects, by collecting more data from, and relating to, the pipeline wall which, in turn, allows more advanced algorithms and software to be used to subsequently generate the defect identification and sizing in the pipelines.

Conventional apparatus is found to have limitations in terms of the sensing of defects particularly, although not exclusively, when used on thick wall grey iron pipeline walls. It is also found that the existing apparatus has problems in being able to identify the width of defects which are detected. It is also known that in certain instances the edges of large defects can be confused and regarded, incorrectly, as small pipe wall defects.

A further problem is that the magnetic saturation of the pipeline wall which is preferred to be achieved in order to allow accurate measurement, cannot always be achieved, especially when the pipeline being checked is relatively large in diameter. If full magnetic saturation is not achieved this can adversely affect the accuracy of the defect sizing which is performed.

A further problem which can be experienced is the manner in which the data which has been obtained is used in order to be able to predict the estimated lifetime of the pipeline which has been checked, in a reliable manner.

An aim of the present invention is to provide an apparatus and method which allows for the improved detection of the condition of the pipeline wall in terms of accuracy of detection and the provision of a more accurate survey of the pipeline wall condition. A further aim is to provide the ability to generate predictions with respect to the estimated lifetime of the pipeline using the data which is obtained.

In a first aspect of the invention there is provided apparatus for the analysis of the condition of at least part of a pipeline wall, said apparatus mountable on the external surface of the pipeline and including a body, means for inducing a magnetic flux into, and at least partially through, the wall of the pipeline adjacent the location of the apparatus and processing means for providing data relating to the said pipeline wall condition and characterized in that said processing mean includes at least one sensor array including a plurality of sensors configured to detect variation in magnetic flux along different respective axes with regard to the wall of the pipeline in order to provide data representative of the condition of the wall of the pipeline.

Typically the at least one sensor array is provided with three sensors in a configuration so as to provide data relating to the magnetic flux in at least three axes with regard to the pipeline wall.

In one embodiment the sensor array is provided as a tri-axial sensor array. In one embodiment the sensors are offset by 90 degrees with respect to each other on the body such that the sensors in each array are located so as to provide measurements with respect to the longitudinal axis, circumferentially and radially respectively relative to the pipe.

In one embodiment the sensors used in the arrays are Hall effect sensors which are transducers that vary their output voltage in response to the detected magnetic field or flux.

In one embodiment a plurality of said sensor arrays are provided at spaced locations on the body of the apparatus and, in one embodiment, each of the sensor arrays are formed by triaxially configured sensors.

Typically, when a change in magnetic flux is detected by at least one of the sensors, analysis of the readings from the sensors in the sensor array provides information showing the length, width and height components of the feature, typically a defect, in the pipeline wall which has caused the change in magnetic flux which has been detected.

In one embodiment the apparatus includes a sensor to provide an indication of the level of magnetic saturation of the pipeline wall. Typically, this sensor is located in front of the sensor arrays with respect to the direction of movement of the body along the pipeline or track on which the body is mounted. The purpose of this sensor is to determine whether or not the pipeline wall is magnetically saturated and/or indicate when it is not magnetically saturated.

In one embodiment this sensor is a Gaussmeter magnetic field sensor.

In a further embodiment the apparatus includes means to measure and/or monitor the distance between the underside of the body of the apparatus and the surface of the pipeline wall along the length of the pipeline wall that the body is moved.

The provision of the distance measurement means allows the effects of pipe wall surface roughness and/or corrosion to be taken into account as these can introduce variations in the distance and hence the air gap between the underside of the body and the pipeline wall surface which, in turn, can introduce signal noise in the inspection tool outputs, and errors in the sizing of the detected defects.

In one embodiment the distance measurement means includes a wheel which contacts the pipeline wall, a gearbox connected to the wheel and a potentiometer.

In one embodiment, the apparatus is provided to be moved around and/or along, a length of pipeline with changes in the magnetic flux and the sensing means being monitored as the apparatus moves along the pipeline.

In one embodiment, the sensing means includes a proximity sensor which is used to detect and determine a change in condition of the pipeline at, or near to, the external surface of the pipeline.

In one embodiment, the apparatus is mounted, and may be provided integrally, on a track, with the track, in turn, being mounted along a section of the pipeline which is to be monitored, said apparatus movable along the track and the track and apparatus can be selectively positioned on the pipeline. The track may be provided with one or more wheels to allow the track to be transportable along with the apparatus mounted thereon.

In one embodiment the track can be positioned at selected locations around the circumference of the length of pipeline so as to allow the survey of the pipeline to be completed for a previously identified portion of the pipeline.

In one embodiment the apparatus body is provided at a spaced distance from the pipeline wall on which the same is provided to be moved along and the body is provided with a plurality of members which extend from the underside of the body to the external surface of the pipeline. Typically the said members are provided in the form of bristles which are flexible along their longitudinal axis.

Typically the bristles are provided to be sufficiently flexible to allow the same to bend down onto the pipeline wall in at least one direction so as to allow the body to be moved along the pipeline in at least one direction and the bristles can then be maintained in contact with the pipeline.

Typically the elongate members are provided to effectively "close" the air gap between the underside of the body and the external surface of the pipeline and thereby increase the ability for the magnetic flux levels achieved by the apparatus to be increased and hence increase the possibility of achieving magnetic saturation of even thicker and/or larger pipeline walls. This, in turn, allows the accuracy of the data which is obtained to be increased.

In a yet further aspect of the invention there is provided apparatus for the analysis of the condition of at least part of a pipeline wall, said apparatus mountable on the external surface of the pipeline and including a body, means for inducing a magnetic flux into and at least partially through the wall of the pipeline adjacent the location of the apparatus and a means for providing data relating to the said pipeline wall condition and characterized in that the apparatus includes a sensor to measure the extent to which the pipeline wall is saturated by the magnetic flux which is generated.

In one embodiment sensors are provided in at least one triaxially mounted sensor array to measure changes in the level of magnetic flux saturation as the apparatus is moved along the pipeline wall.

In a further aspect of the invention there is provided a method for the analysis and detection of changes in condition of at least a portion of a pipeline wall, said method comprising the steps of moving apparatus containing a magnetic flux inductor and sensing means along and/or around a portion of pipeline, inducing a magnetic flux into the pipeline wall, monitoring the readings from the magnetic flux sensing means, identifying changes in the magnetic flux from data received from the sensing means to identify a change in condition of the pipeline wall and wherein the sensing means includes at least one sensor array including a plurality of sensors for detecting the magnetic flux.

In one embodiment the sensor array comprises there sensors each mounted to be angularly offset from the other sensors in the array.

In one embodiment the sensor array comprises three sensors configured to provide data relating to the magnetic flux along three axes. Typically the three axes are such as to provide data relating the length, width and height of the defect which is detected in the pipeline wall.

In one embodiment the method includes retrieving data from detection means which also includes at least one proximity sensor which is used to monitor the change in condition of the external pipeline so changes in the material structure on or near the external surface can be differentiated from changes in condition on the internal surface of the pipeline and hence an accurate indication of the location of the change in condition of the pipeline material is provided. Furthermore, the extent of change in the proximity sensor and also extent of change of magnetic flux can be used to determine the size and depth of the change in condition.

In one embodiment, the pipeline is made from cast iron and the proximity sensor indicates the existence of areas of graphite rather than cast iron material on or near the external surface of the pipeline which would not otherwise be detectable.

Over time, the method includes the step of building a history of faults and defects which are represented by particular detected magnetic flux changes and/or proximity sensor changes and, in the subsequent analysis of new samples of pipeline, reference is made to the historic data to reach a conclusion as to the type and effect of the change in condition represented by detected readings.

In one embodiment ultrasonic readings are performed at a number of locations on the pipeline wall to allow wall thickness outliers to be removed, and local wall thickness patterns to be used in the defect sizing algorithms applied to the magnetic tool outputs.

Typically the data generated from the sensor arrays is processed by processing means using algorithms to determine the characteristics of the pipeline which are represented by the data provided by the sensors.

The use of the sensor arrays, such as the tri-axial sensor array, improves the accuracy of the pipeline inspection which is achieved and, in particular improves the inspection capability in relation to relatively thick walled pipeline and yet further when investigating corrosion on the inner wall face of the pipeline.

In one embodiment faults which have been detected as being internally located faults and which are regarded as lying outside the expected statistical pattern, are identified and an ultrasonic scanner is provided to the location of these faults. From the scan generated from the data from the ultrasonic scanner it can then be identified whether the fault lies on the surface of the internal wall of the pipeline or does in fact lie within the pipeline wall and which is therefore indicative of a fault in the form of a void or slag inclusion and the same can then be accurately assessed.

Specific embodiments of the invention with reference to the accompanying Figures; wherein FIGS. 1a and b illustrate the apparatus of the invention in location on a pipeline in order to survey the same;

The invention is related to the provision of apparatus and a method to allow the detection of changes in condition of the wall of a pipeline to be determined accurately and allow data to be provided which allows the ongoing accurate analysis of the condition of the pipeline wall to be achieved. This can be difficult to achieve especially with cast iron pipelines and yet further with regard to pipelines which have relatively thick walls.

Cast iron material has a number of non-metallic inclusions which can mask smaller defect signals and therefore make it difficult to accurately and reliably detect defects and the metallurgy of these pipes can vary between pipes and across the pipe section thickness. The internal non-metallic inclusions and voids can potentially be identified as internal defects and so it will be appreciated that the accurate detection of defects has conventionally been a significant problem. Furthermore, thick wall pipes are more difficult to fully magnetically saturate and this can result in a reduced repeatability in defect sizing and the wall thickness itself can vary significantly in thick wall castings due to large surface irregularities and eccentrically cast pipe. Also, differences in surface condition, including relatively large areas of shallow corrosion, can influence inspection tool outputs and sizing algorithms and corrosion on the outer face of the pipe can increase the air gap between the inspection heads and the pipe wall in the magnetic circuit.

It is known to be able to utilize mathematical techniques process data from detection apparatus in order to try and allow as accurate a survey of the pipeline wall condition to be provided as possible. However, in each case, the same is reliant upon the accuracy of the initial detection data and therefore the apparatus and method as now described has an aim of trying to identify the means to provide the more accurate data which can subsequently be processed.

Figure 1A:
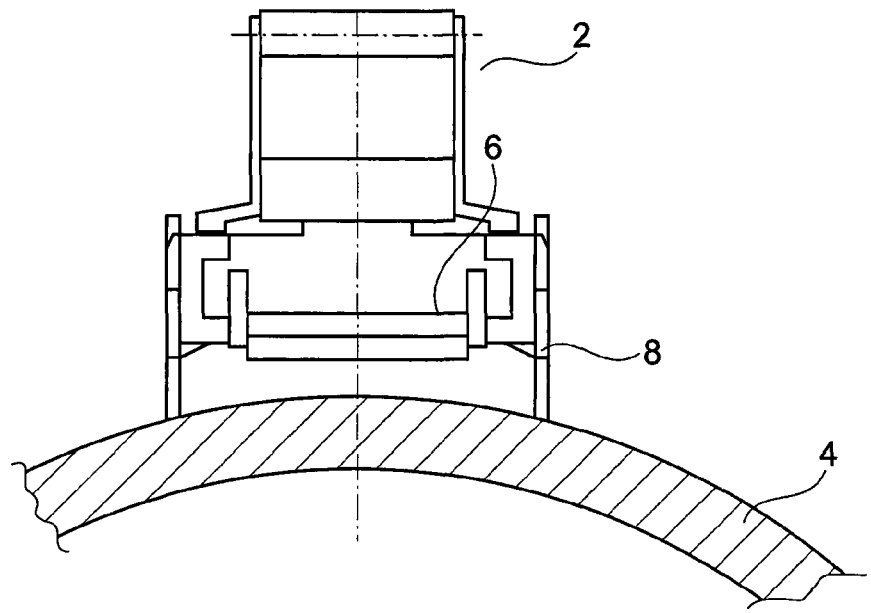
Figure 1B:
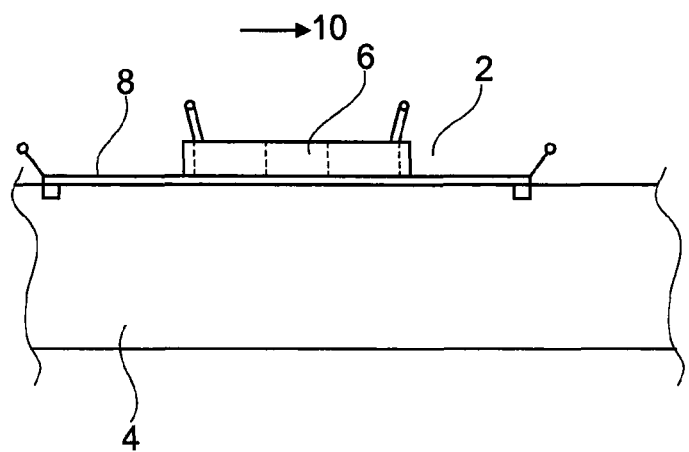

FIG. 1b illustrates in a schematic manner a length of pipeline 4 with the provision of apparatus 2 in accordance with the invention. The end elevation of FIG. 1a shows the apparatus 2 provided in location with regard to part of the pipeline 4 and the apparatus is provided to allow a survey of the condition of at least a portion of the pipeline wall to be achieved. The apparatus is provided with a body 6 which is located on a track or frame 8 which is located with the pipeline in a fixed manner. The body 6 is then provided to be slidable along the track or frame, in this case towards the viewer of the FIG. 1a, and typically along the longitudinal axis of the track 8 as indicated by the arrow 10 in FIGS. 1b and 2 in order to allow the survey to be performed.

Figure 2:
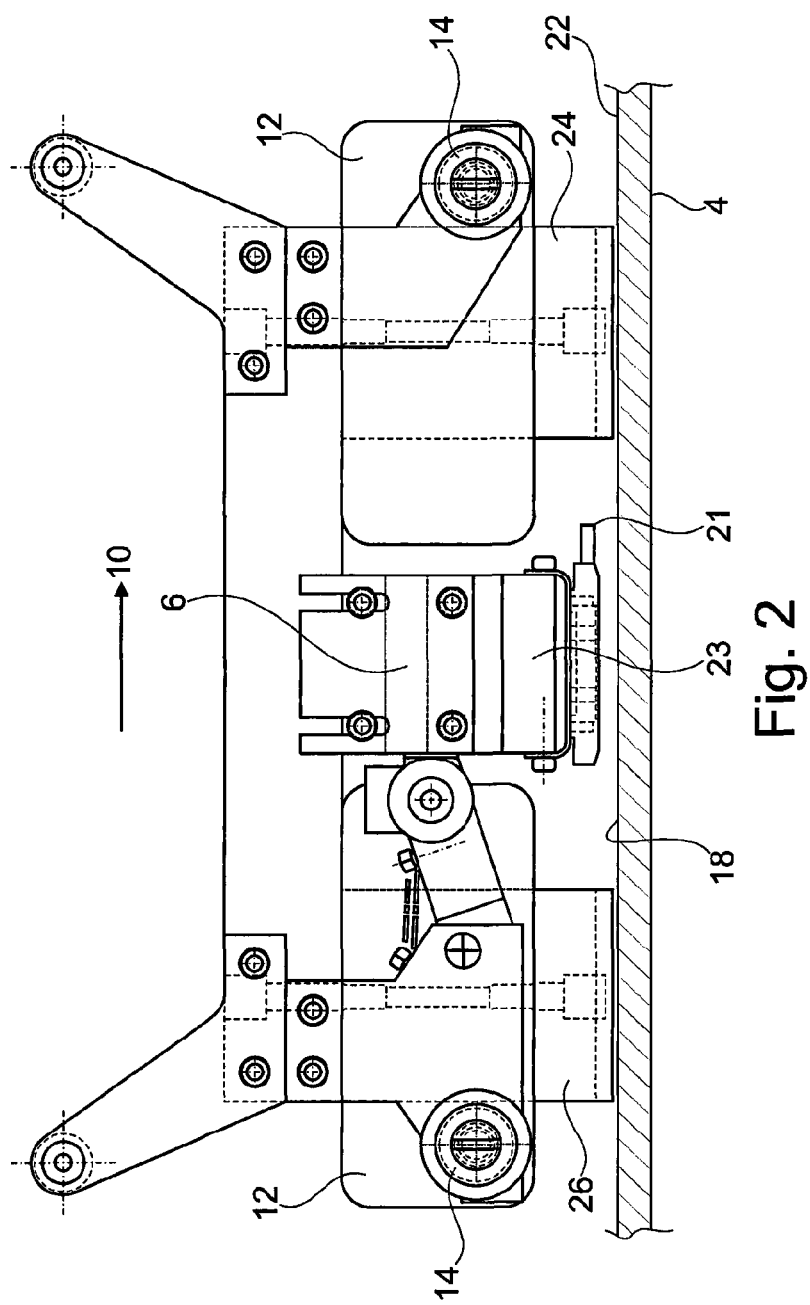
FIG. 2 illustrates the apparatus of FIGS. 1a and b in greater detail and in section.

FIG. 2 illustrates the body 6 of the apparatus in more detail in accordance with the invention. The body is provided with slides 12 which includes a plurality of rollers 14 which engage with the said track or frame 8 (not shown in FIG. 2) and which allow the body to be moved along the same in the direction 10.

There is provided an air gap 18 between the underside of the body 6 and the external face 22 of the pipeline 4. It is found that this air gap can mean that magnetic saturation is not achieved through the depth of the pipeline wall and this can introduce errors when defect sizing algorithms are utilized using the data form the apparatus. Where saturation is not achieved then carrying out calibration scans on pipes of the same pipe wall thickness with machined defects, can improve sizing accuracy and, since the inspection data is held after reporting, this can be carried out retrospectively. However in order to further improve the survey as it occurs, the body 6, as shown in FIG. 2, is provided with a sensing means 21 mounted in advance of the same with regard to the direction of movement 10. This sensing means, typically a Gaussmeter, detects whether or not the pipeline wall is saturated and monitors the same as the body is moved along the pipeline wall.

The provision of the additional sensor 21 to measure the pipeline wall magnetic flux saturation allows a feedback loop to be utilized to optimize the required electro-magnetic coil current, based on controlling the level of the air-coupled flux running parallel to the pipe wall. The sensor 21 is mounted in a non ferrous cover directly in front of the inspection head 23 and at the appropriate orientation to measure the air coupled flux running parallel to the pipeline wall.

In addition, or alternatively, and not shown, a series of elongate members in the form of bristles can be provided to depend outwardly from the tool body and towards the external face of the pipeline wall 22 to contact the same. The inclusion of the bristles eliminates the air gaps between the magnetic poles of the flux inducing means in the body and hence allow higher saturation of the pipeline wall to be achieved and hence improve saturation through the portion of the pipeline wall which is being surveyed.

The apparatus shown in FIG. 2 provides two shoes 24,26 for inducing the magnetic field from one of the shoes 24 into the pipeline wall and then back through the shoe 26. Typically the shoes are connected to electromagnets provided in the apparatus which allow the magnetic field to be induced and typically the dimension of the shoes are such as to be substantially the same width as the electromagnets so as to reduce the air flux influence.

It is also necessary to allow the shoes to be changed so as to allow the apparatus to be adapted to be used with pipelines of differing diameters and/or to allow sensors to be removed and replaced as required. In order to accommodate this and allow the change to be made relatively quickly, the apparatus, in one embodiment, is provided in connection with the frame 8 along which the same travels and the frame can simply be turned over and access gained to replace the shoes and/or sensors as required. This avoids the conventional need of having to substantially dismantle the apparatus to achieve the changes and/or to perform general maintenance.

Figure 5:
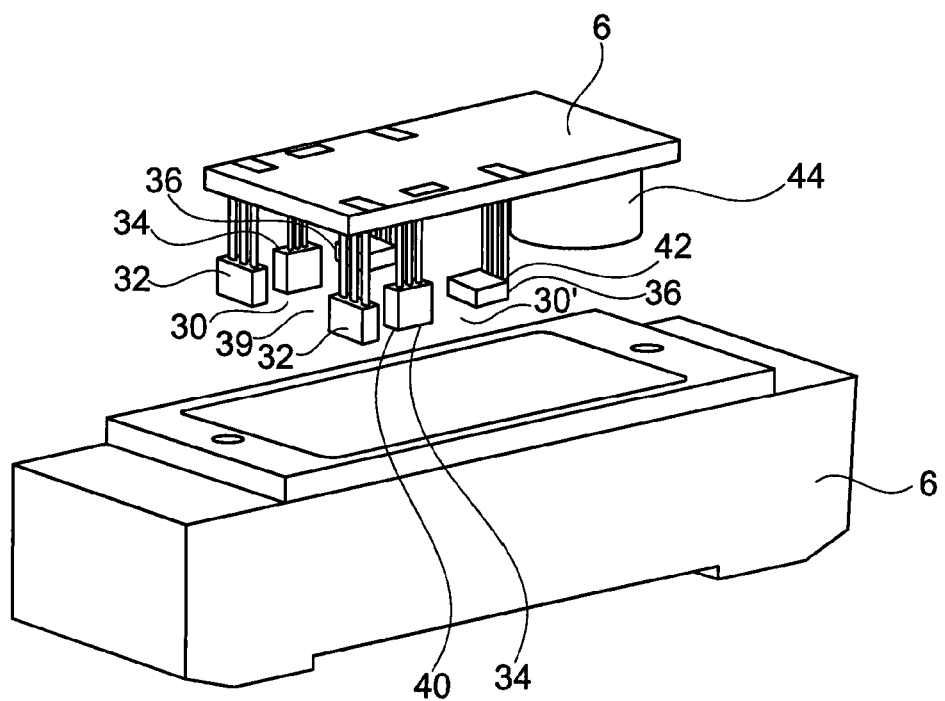
FIG. 5 illustrates the sensor array which provides the information illustrated in FIGS. 3 and 4.

There is illustrated in FIG. 5 two sensor arrays 30, 30' which are provided within the body 6 and at the inspection head 23. The sensors provided in each array are typically Hall effect sensors, which allow the detection of the magnetic flux in the pipeline wall which underlies the inspection head 23 and detects changes in the same in order to allow the data therefore to be used to indicate the presence of defects in the pipeline wall. In accordance with the invention, each sensor array 30 includes three Hall sensors, 32,34,36 as shown in FIG. 5. It will be seen that the respective longitudinal axes 38, 40,42 of each of the sensors is arranged at a 90 degrees offset with respect to the other sensors in the array and this allows a three dimensional array of data signals to be received from the combination of sensors in each sensor array.

Figure 3A:
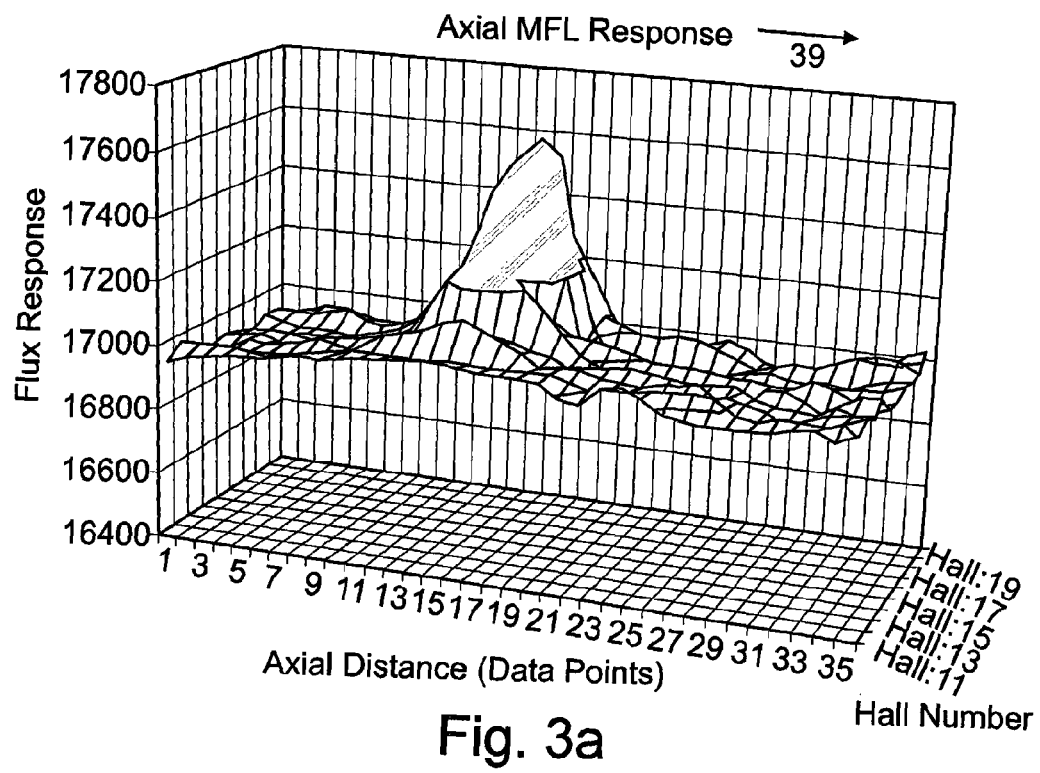
FIGS. 3 and 4 illustrate the information which is received from a sensor array in accordance with one embodiment of the invention.
Figure 3B:
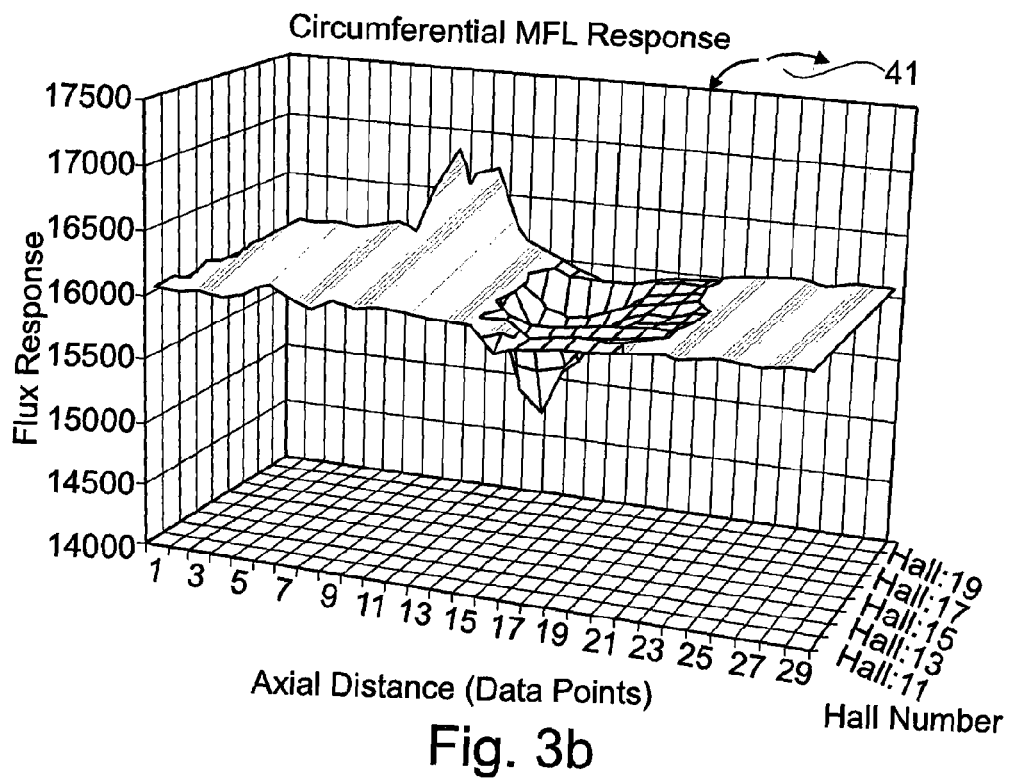
Figure 3C:
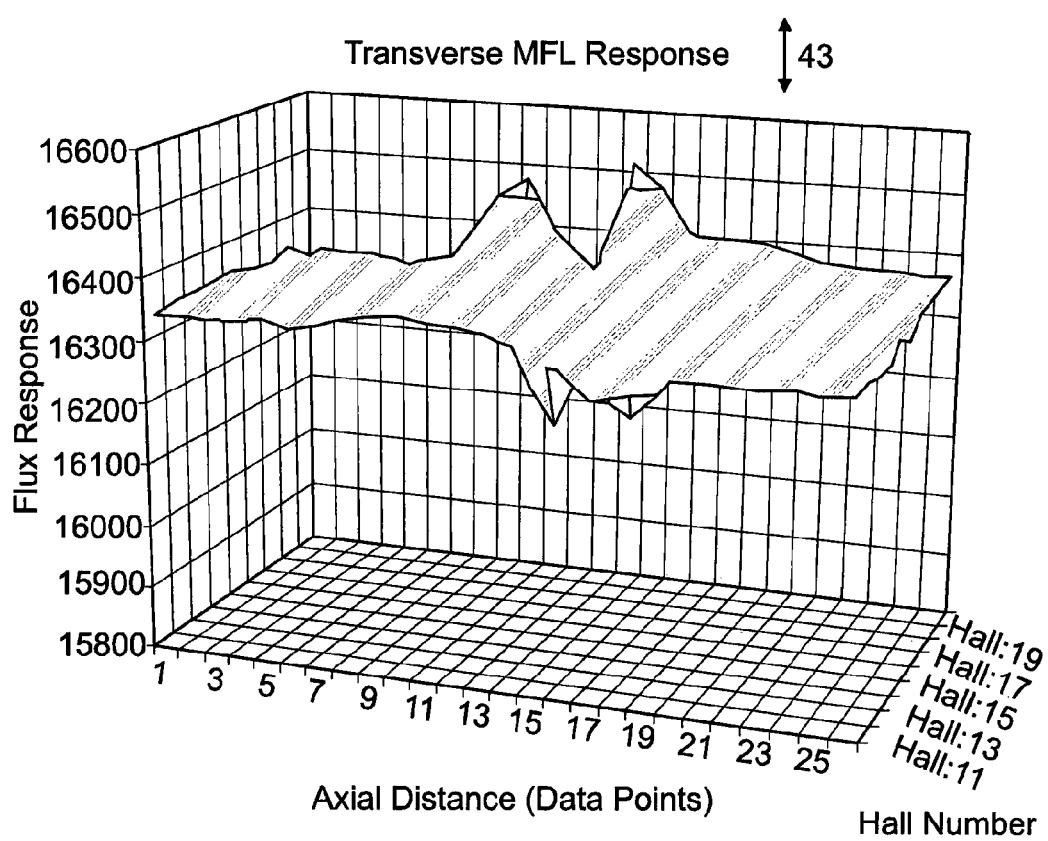

The three dimensional data signals which are received from the sensors in each array are illustrated in FIG. 3. FIG. 3a indicates the plot obtained from data from a sensor in the array for along the pipeline in the direction of arrow 39, FIG. 3b indicates the circumferential plot obtained from the data from the sensor array in the direction of arrow 41 and FIG. 3c indicates the transverse plot obtained from data from the sensor array in the direction of arrow 43, all with respect to the pipeline which is being analysed and the length of which extends parallel with the arrow 39.

Figure 4:
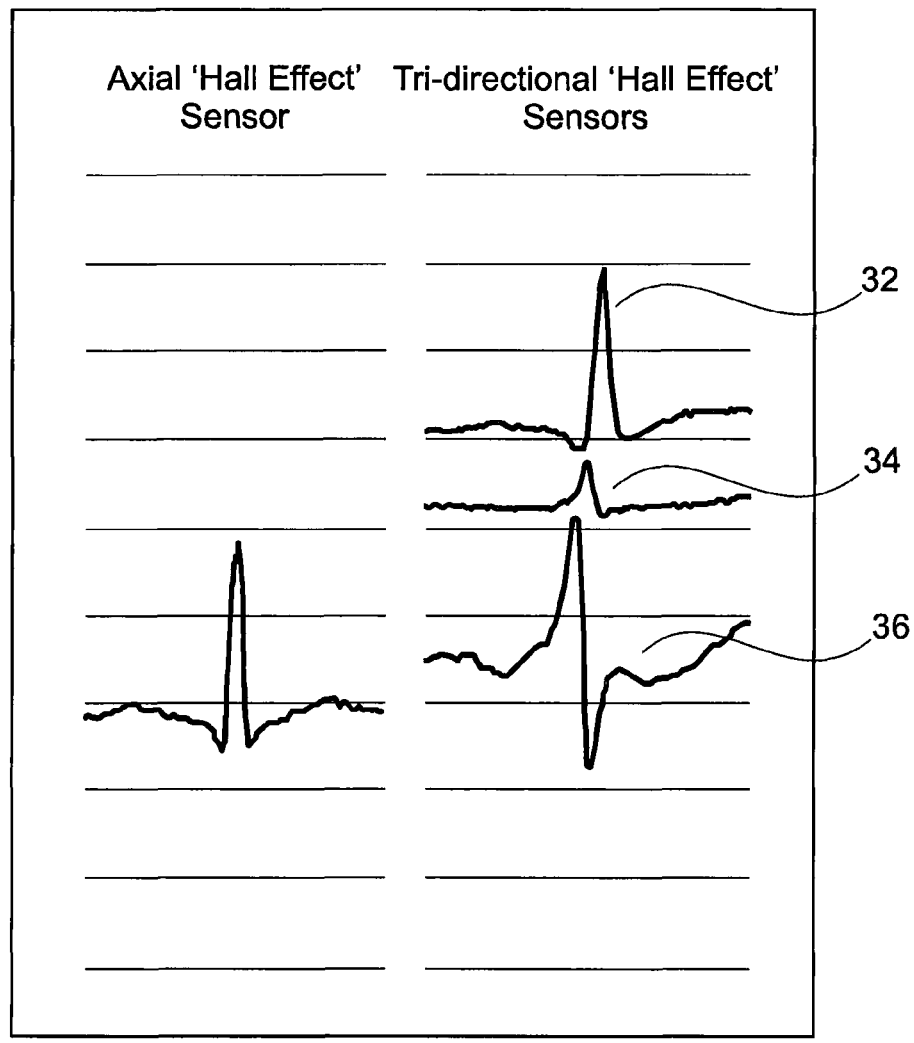

In FIG. 4 there is illustrated on the right hand side the graphical plots received from the sensor array 30 in accordance with the invention and on the left hand side, a single graphical plot which would received from a conventional, single Hall effect sensor containing apparatus and so it is seen by providing the triaxial sensor array of the current invention so a significantly greater level of detail can be provided and therefore a finer granularity of analysis and detection of the defects in the pipeline. Each sensor array 30, in this embodiment, provides three signal outputs which, when a defect is detected as existing in the pipeline wall due to changes in the detected magnetic flux, also then allow the length, width and height of the defect to be identified from the three different axial data readings obtained from the sensors in the array. As the sensors in each array are closely located each sensor in the array will pass in the same plane through the magnetic flux "bulge" which is created when a defect in the pipeline wall is present and so the sensors provide data which relate to the length, width and height of the "bulge" respectively. Analysis software can then be used to take into account the slight longitudinal offset of the three sensors positions in the array and any effect that this has on the reading from the respective sensors.

Figure 6:
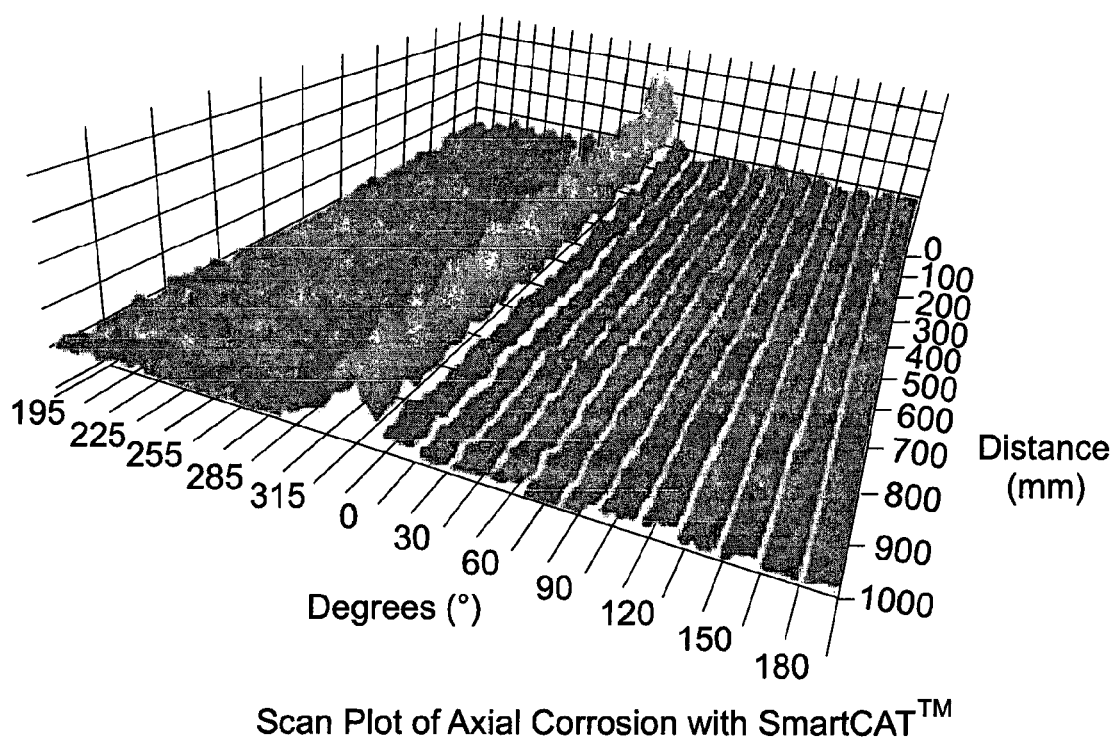
FIG. 6 illustrates a scan plot which can be achieved using the sensor arrays in accordance with one embodiment of the invention.

The provision of the sensor arrays in accordance with the invention greatly improves defect identification and the subsequent accuracy of the defect sizing processes. The provision in each array of the sensors being installed at different angles to the magnetic flux and, in particular to the flux conditions when a defect is present in the pipeline wall, provides a greater level of information on magnetic flux leakage patterns. An example of this is illustrated in the plot illustrated in FIG. 6 which relates to and is identified as a relatively long, narrow, defect in the pipeline wall in accordance with the invention.

Thus, the provision of the sensor arrays provides improvement in the signals obtained as a result of the displaced flux resulting from pipe wall defects by allowing the measurement of depth, width and length and this, in conjunction with the proximity sensors, which allow the identification of whether the identified defect is on internal or external surface of the pipeline wall provides a significant improvement in the accuracy of the data which is obtained. The proximity sensor 44 is shown in FIG. 5 and this allows the determination of whether the defect detected by the sensors array 30 is located on the exterior or interior of the pipeline wall as if the proximity sensor changes then the defect is deemed to be at the external surface of the pipeline wall and if the defect is identified by the sensor array as being present but the proximity sensor condition does not change then the defect is determined to be internal or at the internal face of the pipeline wall. In either case the data from the sensors in the sensor array can be used to determined, the length, width and depth of the defect.

In one embodiment there is the possibility that a fault in the pipeline wall which is detected may be indicated as being located on the interior surface of the wall whereas in fact the fault is actually within the wall. This is most likely to occur when the apparatus is used for the detection of faults in relatively thick walled pipes. In this case, once the analysis using the apparatus as herein described has been performed, faults which have been detected and which are regarded as lying outside the expected statistical pattern, are identified and an ultrasonic scanner is provided to the location of these faults. From the scan generated from the data from the ultrasonic scanner it can then be identified whether the fault lies on the surface of the internal wall of the pipeline or does in fact lie within the pipeline wall and which is therefore indicative of a fault in the form of a void or slag inclusion and the same can then be accurately assessed.

In one embodiment, when the apparatus is to be used in relatively hazardous pipeline analysis such as pipelines used to carry gas, the electrical safety is paramount. In this case the apparatus is provided such that there are no electrical connectors directly mounted on the body of the tool and instead a socket may be provided at the end of the track of the apparatus with which a connector connected to the power supply can be connected and locked in position. This allows the cable to be supplied to the body as required but with no electrical connections provided on the body. Furthermore the body itself can be provided with a cavity in which the electronic processing and control apparatus is located and said cavity is purged with a gas such as hydrogen and maintained with hydrogen therein so as to prevent the risk of sparks or other combustion occurring and thereby allowing the apparatus to be used in hazardous environments.

With respect to the analysis of the data which has been obtained using the apparatus, the same can be used to determine an estimate of the likely lifetime of the pipeline which has been monitored. The failure can be considered to occur when the corrosion has proceeded to an extent that the average remaining wall thickness in a pipeline section has reduced to the critical thickness depth tc. The corrosion much material is lost that the average wall thickness of the 1 meter length is predicted to reach the critical wall thickness everywhere.

The table below shows a model generated using data obtained from the monitoring of a pipeline length and the model incorporates a depth corrosion rate time^0.5 and width corrosion rate which is linear with time.

| age of pipe at which total pit corrosion to be assessed | pit depths to be counted | estimated pit count at each depth | Approximate number of pits of this depth | Estimated radius of pits, based on linear corrosion rate with time | estimated volume each pit assumed conical (⅓ pi r^2 h)mm^3 | total volume of pits of that depth |
|---|---|---|---|---|---|---|
| 40 | 1 | 400.0 | 88.5 | 6 | 42 | 3707 |
| | 1.5 | 311.5 | 68.9 | 9 | 141 | 9745 |
| | 2 | 242.6 | 53.7 | 13 | 335 | 17991 |
| | 2.5 | 188.9 | 41.8 | 16 | 654 | 27368 |
| | 3 | 147.1 | 32.6 | 19 | 1131 | 36831 |
| | 3.5 | 114.5 | 25.4 | 22 | 1796 | 45546 |
| | 4 | 89.2 | 19.7 | 25 | 2681 | 52942 |
| | 4.5 | 69.4 | 15.4 | 28 | 3817 | 58696 |
| | 5 | 54.0 | 12.0 | 32 | 5236 | 62690 |
| | 5.5 | 42.1 | 9.3 | 35 | 6969 | 64963 |
| | 6 | 32.7 | 7.3 | 38 | 9048 | 65659 |
| | 6.5 | 25.5 | 5.6 | 41 | 11503 | 64986 |
| | 7 | 19.8 | 4.4 | 44 | 14368 | 63180 |
| | 7.5 | 15.4 | 3.4 | 47 | 17671 | 60486 |
| | 8 | 12.0 | 2.7 | 51 | 21447 | 57134 |
| | 8.5 | 9.3 | 2.1 | 54 | 25724 | 53334 |
| | 9 | 7.3 | 1.6 | 57 | 30536 | 49269 |
| | 9.5 | 5.7 | 1.3 | 60 | 35914 | 45091 |
| | 10 | 4.4 | 1.0 | 63 | 41888 | 40923 |
| | 10.5 | 3.4 | 0.8 | 66 | 48490 | 36860 |
| | 11 | 2.7 | 0.6 | 70 | 55753 | 32973 |
| | 11.5 | 2.1 | 0.5 | 73 | 63706 | 29311 |
| | 12 | 1.6 | 0.4 | 76 | 72382 | 25907 |
| | 12.5 | 1.3 | 0.3 | 79 | 81812 | 22778 |
| | 13 | 1.0 | 1.0 | 82 | 92028 | 89611 |
| | 13.5 | 0.8 | 0.8 | 85 | 103060 | 78035 |
| | 14 | 0.6 | 0.6 | 89 | 114940 | 67671 |
| | 14.5 | 0.5 | 0.5 | 92 | 127701 | 58456 |
| | 15 | 0.4 | 0.4 | 95 | 141372 | 50312 |
| | 15.5 | 0.3 | 0.3 | 98 | 155985 | 43156 |
| | 16 | 0.2 | 0.2 | 101 | 171573 | 36900 |
| | 16.5 | 0.2 | 0.2 | 104 | 188166 | 31456 |
| sum of the volume of all pits in 1 metre length mm^3 | | | | | | 1483967.49 |
| surface area of pipe 1 metre long, mm^2 | | | | | | 1570796.33 |
| effective loss of wall surface, mm | | | | | | 0.94 | process for the pipeline can then be modelled as an extreme value distribution, based on observed pits or faults over a 1 meter length. The user can then select to model Pit depth growth rates as a power law say proportional to the time^0.5 and the pit width growth rates may also be modelled, and a linear rate directly proportional to time can be applied. When a distribution model has been fitted to the data, it may be applied to calculate the total number of pits of each depth within an area of interest, say a 1 meter length.

Using the equation:

$$i_t = M \times \left| \frac{(d - \xi_t)}{\left(\frac{\alpha_a t^b}{k}\right)} \right|^{1/k}$$

Figure 7:
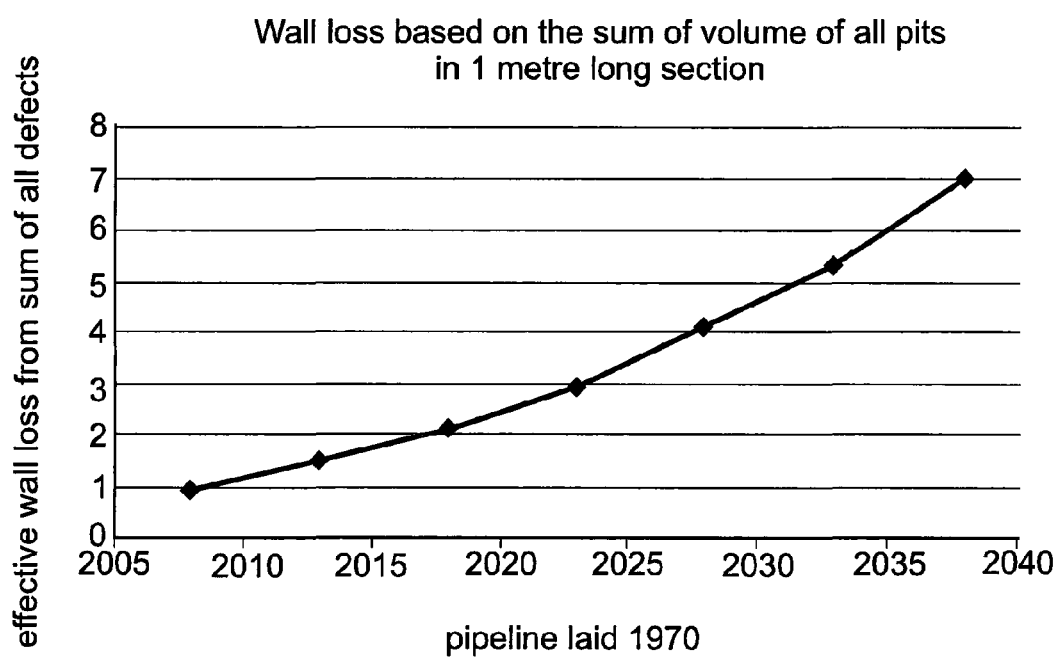
FIG. 7 indicates the pipeline life estimation calculated in accordance with one embodiment of the invention.

The width and volume of all these pits may be estimated, and the total volume of material lost to corrosion derived. This volume, applied over the area of the 1 meter length gives an estimate of net wall thickness loss. This calculation can be applied at times into the future to estimate the likely increase in pit size and total corroded volume. Eventually so The calculations may be repeated at times into the future, giving the results indicated in FIG. 7. In the results shown in FIG. 7 and the table above the pipe wall is about 16 mm and tc about 10 mm, so an average wall loss of 6 mm would indicate failure, in 2035. So in summary, failure may be predicted based on the integration of all predicted pit corrosion over the 1 meter length. Extrapolation over longer lengths will give much the same result, because we are looking at a process more related to the 'average' condition of the asset, estimating the arrival at a state where the entire pipe area is substantially degraded. It should also be noted that while the average value does not change as more samples are analysed the estimate of the average improves, whereas the likelihood of a single deep value occurring, does increase as more surface is considered.

There is therefore provided in accordance with the invention apparatus which can be used to provide accurate detection of defects in pipeline walls without the need to place the apparatus internally of the pipeline.

The invention claimed is:
1. Apparatus for the analysis of the condition of at least part of a pipeline wall, said apparatus comprising:

a track on an external surface of the pipeline and on which a body is mountable and movable therealong, a body including a first shoe for inducing a magnetic flux into an air gap between the underside of the body and the external face of the pipeline, and at least partially through, the wall of the pipeline adjacent the location of the apparatus and then back through a second shoe of the body, spaced from the first shoe, and processing means for providing data relating to the magnetic flux in the wall of said pipeline at different locations of the pipeline wall as the apparatus is moved with respect thereto and a proximity sensor to detect and determine a change in condition of the pipeline at, or near to, the external surface of the pipeline and said processing means includes a plurality of sensor arrays within the body and at an inspection head located such that the said magnetic flux induced into the pipeline wall underlies the inspection head, each of said arrays including three sensors configured in a tri-axial sensor array to detect variation in magnetic flux in at least three axes with regard to the wall of the pipeline at the said different locations in order to provide data representative of the condition of the wall of the pipeline.

2. Apparatus according to claim 1 wherein said sensors in the tri-axial array are offset by 90 degrees with respect to each other on the body to provide measurements with respect to the longitudinal axis, circumferentially and radially respectively relative to the pipe.

3. Apparatus according to claim 1 wherein the sensors used in the array are Hall effect sensors.

4. Apparatus according to claim 1 wherein the plurality of said sensor arrays are provided at spaced locations on the body of the apparatus.

5. Apparatus according to claim 1 wherein the data from the sensors in each sensor array is passed to the processing means for analysis and changes in the data is used to provide information showing the length, width and height components of a defect detected in the pipeline wall which has caused the change in magnetic flux data.

6. Apparatus according to claim 1 wherein the apparatus includes a sensor to provide an indication of the level of magnetic flux saturation of the pipeline wall.

7. Apparatus according to claim 6 wherein the sensor is located between an end of the body and one of the sensor arrays.

8. Apparatus according to claim 7 wherein the said sensor is a Gaussmeter magnetic field sensor.

9. Apparatus according to claim 1 wherein the apparatus includes means to measure and monitor the distance between the underside of the body of the apparatus and an external surface of the pipeline wall and detect variations in the distance and air gap between the underside of the body and the pipeline wall.

10. Apparatus according to claim 9 wherein the distance measurement means includes a wheel which contacts the pipeline wall, a gearbox connected to the wheel and a potentiometer.

11. Apparatus according to claim 1 wherein the track is provided with one or more wheels to allow the track to be transportable along with the body mounted thereon.

12. Apparatus according to claim 1 wherein the apparatus includes another pipe with the same pipe wall thickness as the at least part of the pipeline wall and said body, sensor arrays and proximity sensor are used to perform calibration scans of said pipe.

13. A method for the analysis and detection of changes in condition of at least a portion of a pipeline wall, said method comprising the steps of:

moving apparatus containing a magnetic flux inductor and sensing means along and/or around a portion of pipeline;

inducing a magnetic flux into an air gap between the underside of the body and the external face of the pipeline, and at least partially through the wall of the pipeline adjacent the location of the apparatus and then back through a second shoe of the body, spaced from the first shoe;

monitoring the readings from the magnetic flux sensing means; and identifying changes in the magnetic flux from data received from the sensing means to identify a change in condition of the pipeline wall and wherein the sensing means includes a proximity sensor and at least first and second sensor arrays, each including at least three sensors mounted in a tri-axial array for detecting magnetic flux; and using the sensing means to perform a calibration scan on another pipe of the same pipe wall thickness as the portion of the pipeline wall.

14. A method according to claim 13 wherein each sensor array provides data relating to the magnetic flux along three axes to provide data relating to the length, width and height of a defect which is detected in the pipeline wall.

15. A method according to claim 13 wherein the method includes retrieving data from the proximity sensor used to monitor the change in condition of the external pipeline so changes in the material structure on or near the external surface can be differentiated from changes in condition on the internal surface of the pipeline and hence an accurate indication of the location of the change in condition of the pipeline material is provided.

16. A method according to claim 15 wherein the extent of change in the proximity sensor and also extent of change of magnetic flux can be used to determine the size and depth of the change in condition.

17. A method according to claim 13 wherein a history of faults and defects which are represented by particular detected magnetic flux changes and/or proximity sensor changes is built and, in the subsequent analysis of new samples of pipeline, reference is made to the historic data to reach a conclusion as to the type and effect of the change in condition represented by detected readings.

18. A method according to claim 13 wherein the apparatus is moved around and/or along, a length of pipeline with changes in the magnetic flux and the sensing means being monitored as the apparatus moves around and/or along the pipeline.

19. Apparatus for the analysis of the condition of at least part of a pipeline wall, said apparatus comprising:

a track on an external surface of the pipeline and on which a body is mountable and movable therealong;

the body including a first shoe for inducing a magnetic flux into an air gap between an underside of the body and an external face of the pipeline and at least partially through the wall of the pipeline adjacent a location of the apparatus and then back through a second shoe of the body, spaced from the first shoe; and processing means for providing data relating to the magnetic flux in the wall of said pipeline at different locations of the pipeline wall as the body is moved with respect thereto and a proximity sensor to detect and determine a change in condition of the pipeline at, or near to, the external surface of the pipeline and said processing means includes a plurality of sensor arrays within the body and at an inspection head located such that the magnetic flux induced into the pipeline wall underlies the inspection head, each of said arrays including three sensors configured in a tri-axial sensor array to detect variation in magnetic flux in at least three axes with regard to the wall of the pipeline at the different locations in order to provide data representative of a condition of the wall of the said pipeline; and said apparatus includes another pipe with the same pipe wall thickness as the said part of the pipeline wall and said body, sensor arrays and proximity sensors are used to perform calibration scans of said pipe wall.

* * * * *